US007173013B2

(12) United States Patent
Kolobov et al.

(10) Patent No.: US 7,173,013 B2
(45) Date of Patent: Feb. 6, 2007

(54) TREATMENT OF TUBERCULOSIS USING IMMUNOMODULATOR COMPOUNDS

(75) Inventors: Alexandr A. Kolobov, Sestroretsk (RU); Andrey S. Simbirtsev, St. Petersburg (RU); Tat'yana I. Vinogradova, Tosno (RU); Natal'ya V. Zabolotnyh, St. Petersburg (RU)

(73) Assignee: SciClone Pharmaceuticals, Inc., San Mateo, CA (US)

( * ) Notice: Subject to any disclaimer, the term of this patent is extended or adjusted under 35 U.S.C. 154(b) by 66 days.

(21) Appl. No.: 10/485,487

(22) PCT Filed: Dec. 20, 2001

(86) PCT No.: PCT/US01/48560

§ 371 (c)(1),
(2), (4) Date: Aug. 16, 2004

(87) PCT Pub. No.: WO03/013572

PCT Pub. Date: Feb. 20, 2003

(65) Prior Publication Data

US 2004/0259806 A1 Dec. 23, 2004

(30) Foreign Application Priority Data

Aug. 6, 2001 (RU) ............................. 2001115900

(51) Int. Cl.
*A61K 38/02* (2006.01)
*A61K 38/05* (2006.01)
*C07K 2/00* (2006.01)
*C07K 5/037* (2006.01)

(52) U.S. Cl. ............................ 514/19; 514/2; 530/332; 548/495

(58) Field of Classification Search ..................... None
See application file for complete search history.

(56) References Cited

U.S. PATENT DOCUMENTS 4,520,196 A 5/1985 Wei ............................ 544/285
5,212,192 A 5/1993 Raeymaekers et al. ..... 514/368
5,916,878 A 6/1999 Kolobov et al. .............. 514/19
6,060,452 A 5/2000 Green et al. .................. 514/19
6,124,098 A * 9/2000 Heym et al. .................... 435/6
6,509,151 B1 * 1/2003 Riley ............................ 435/6

FOREIGN PATENT DOCUMENTS

WO WO 94/20063 A2 9/1994
WO WO 97/19691 A1 6/1997
WO WO 97/21444 A1 6/1997

OTHER PUBLICATIONS

Database Imsdrugnews, R & D Focus Drug News, XP-002377619, Sep. 6, 1999.
Database Cin, Other Research News, XP-002377620, Feb. 28, 2000.
Database Imsdrugnews, R & D Focus Drug News, XP-002377621, Jan. 22, 2001.

* cited by examiner

*Primary Examiner*—Jeffrey Edwin Russel
(74) *Attorney, Agent, or Firm*—Rothwell, Figg, Ernst & Manbeck, P.C.

(57) ABSTRACT

Tuberculosis in an animal is treated by administration of a therapeutically effective amount of an immunomodulator of formula A. In formula (A), n is 1 or 2, R is hydrogen, acyl, alkyl or a peptide fragment, and X is an aromatic or heterocyclic amino acid or a derivative. The animal may be a mammal such as a human (A)

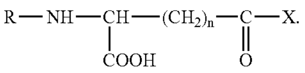

14 Claims, No Drawings

TREATMENT OF TUBERCULOSIS USING IMMUNOMODULATOR COMPOUNDS

REFERENCE TO RELATED APPLICATIONS

This application is a 371 national phase of PCT/US01/48560, filed Dec. 20, 2001, which claims priority from Russian Federation Application 2001-115900, filed Aug. 6, 2001.

BACKGROUND OF THE INVENTION

1. Field of the Invention

The present invention relates generally to a method for treating tuberculosis in animals, including mammals such as humans.

2. Description of the Related Art

Tuberculosis is a chronic, infectious disease that is caused by infection with tubercle bacilli belonging to the *Mycobacterium* genus. The infection may be asymptomatic for a period of time, but the most common manifestations include chronic inflammation of the lungs resulting in fever and respiratory symptoms. If left untreated, significant morbidity and death can occur. Tuberculosis strikes people of all ages but is more common among the elderly and immunosuppressed individuals. The disease can afflict animals, including humans, and livestock such as cattle, hogs, and poultry. *Mycobacterium tuberculosis* is the most common cause of human tuberculosis, but a number of cases are due to *Mycobacterium bovis*. Animal tuberculosis in industrialized countries is controlled with milk pasteurization; as a result, such actions drastically reduce the incidence of disease caused by *M. bovis* in both cattle and humans. On the other hand, developing countries do not implement control measures consistently and pasteurization is rarely practiced.

Methods of prevention, detection, diagnosis, and treatment have greatly reduced both the number of people who contract the disease and the number of people who die from it. Known therapies in the art include isoniazid (isonicotinic acid hydrazide), rifampicin pyrazinamide (PZA), kanamycin, ethambutol, streptomycin, capreomicin, amicacin and cycloserine. Isoniazid is still a front-line therapy against tuberculosis and modern short-course chemotherapy is initiated with three drugs: isoniazid, rifampicin and PZA. Although tuberculosis can generally be controlled using extended antibiotic therapy, this treatment is usually an insufficient method for prevention of the spread of the disease.

Although certain chemotherapy and vaccine protocols have become available for the treatment of tuberculosis, the disease continues to claim more lives per year than any other infectious disease. There remains a need in the art for improvements in the prevention and treatment of tuberculosis.

BRIEF SUMMARY OF THE INVENTION

In accordance with the present invention, tuberculosis in an animal, such as a mammal, e.g., human, is treated by administration of a therapeutically effective amount of an immunomodulator of Formula A:

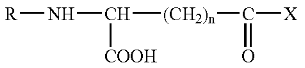

(A)

In Formula A, n is 1 or 2, R is hydrogen, acyl, alkyl or a peptide fragment, and X is an aromatic or heterocyclic amino acid or a derivative thereof.

DETAILED DESCRIPTION OF THE PREFERRED EMBODIMENTS

As noted above, the present invention is generally related to a method for treatment of tuberculosis in mammals through the administration of a therapeutically effective amount of an immunomodulator. The immunomodulator is illustrated by Formula A.

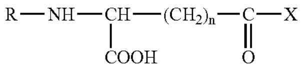

(A)

In Formula A, n is 1 or 2, R is hydrogen, acyl, alkyl or a peptide fragment, and X is an aromatic or heterocyclic amino acid or a derivative thereof, preferably where=L-tryptophan or D-tryptophan. Appropriate derivatives of the aromatic or heterocyclic amino acids for "X" are: amides, mono-or di-(C1–C6) alkyl substituted amides, arylamides, and (C1–C6) alkyl or aryl esters. Appropriate acyl or alkyl moieties for "R" are: branched or unbranched alkyl groups of 1 to about 6 carbons, acyl groups from 2 to about 10 carbon atoms, and blocking groups such as carbobenzyloxy and t-butyloxycarbonyl. Preferably the carbon of the CH group shown in Formula A has a stereoconfiguration, when n is 2, that is different from the stereoconfiguration of X.

Preferred embodiments utilize compounds such as γ-D-glutamyl-L-tryptophan, γ-L-glutamyl-L-tryptophan, γ-L-glutamyl-$N_{in}$-formyl-L-tryptophan, N-methyl-γ-L-glutamyl-L-tryptophan, N-acetyl-γ-L-glutamyl-L-tryptophan, γ-L-glutamyl-D-tryptophan, β-L-aspartyl-L-tryptophan, and β-D-aspartyl-L-tryptophan. Particularly preferred embodiments utilize γ-D-glutamyl-L-tryptophan, sometimes referred to as SCV-07. These compounds, methods for preparing these compounds, pharmaceutically acceptable salts of these compounds and pharmaceutical formulations thereof are disclosed in U.S. Pat. No. 5,916,878, incorporated herein by reference.

The Formula A compounds may be administered as dosages in the range of about 0.001–10 mg. Dosages may be administered one or more times per week, preferably on a daily basis, with dosages administered one or more times per day. In preferred embodiments, the dosages are administered by intramuscular injection, although other forms of injection and infusion may be utilized, and other forms of administration such as oral or nasal inhalation or oral ingestion may be employed.

In preferred embodiments, the compounds of Formula A are administered at a dosage within a range of about 0.01–1 mg, more preferably at a dosage of about 0.1 mg.

Dosages may also be measured in micrograms per kilogram, with dosages in the range of about 0.001–10 micrograms per kilogram, more preferably within the range of about 0.01–1 micrograms per kilogram, and most preferably at about 0.1 micrograms per kilogram.

The method of treating tuberculosis with an immunomodulator of Formula A may further include administration of a therapeutically effective amount of an antimicrobial or bacteriostatic compound effective against tuberculosis. Suitable tuberculosis-treating antimicrobial or bacteriostatic compounds include isoniazid, pyrazinamid, rifampicin, kanamycin, ethambutol, streptomycin, capreomicin, amicacin and cycloserine. These compounds may be administered with dosages within a range of about 100–10,000 mg, preferably within the range of about 200 to 2,000 mg, more preferably within the range of about 400 to 1,000 mg. A compound of Formula A may be administered concurrently and/or sequentially with administration with one or more of the tuberculosis-treating antimicrobial or bacteriostatic compounds, e.g., administered prior to, during, and/or subsequent thereto.

In addition, the Formula A compounds may be used in the preparation of a medicament for the treatment of tuberculosis. Preferably, the Formula A compounds are in a composition including a pharmaceutically acceptable carrier.

The following examples are offered by way of illustration and not by way of limitation.

EXAMPLE 1

A patient, born in 1955 was admitted to the hospital with infiltrative tuberculosis with destruction and dissemination in the upper lobe of the left lung. In addition to tuberculosis, the patient had a duodenal ulcer, chronic bronchitis and multivalent allergy. Lymphopenia (18%) and increased ESR (25 mm/h) were present in the blood count. A decrease in the CD3+ subset was also indicated and infiltrate with a cavity and foci of dissemination were observed in the axilar segment of the left lung. Aggressive traditional antituberculosis therapy was carried out including isoniazid at 600 mg/day intravenously, pyrazinamid at 1500 mg/day per os, rifampicin at 450 mg/day per os.

The traditional therapy was unsuccessful, and SCV-07 treatment was undertaken. Following a course of SCV-07 therapy at 0.1 mg daily for 5 days, bacterial intoxication resolved, destructive cavities closed and the sputum culture test was negative. CD3+ lymphocytes increased and tolerance to other drugs improved. Immune complexes in circulation decreased close to normal (from 84 U to 69 U, normal level is 22–66 U).

EXAMPLE 2

A patient born in 1962 was admitted to the hospital with infiltrative tuberculosis, destructive phase in the upper lobe and 6th segment of the right lung and 4–5th segments of the left lung. Prior to SCV-07 therapy, symptoms of bacterial intoxication, dyspnea and rales above the damaged lobes were present. During tomographic examination, multiple destructive cavities on the infiltrative background were observed in the upper lobe and gross-focus dissemination in the 6th segment of the right lung were observed as well. Large foci of lung destruction surrounded by perifocal inflammation were found in the lingual lobe of the left lung. Furthermore, leukocytosis ($11.4\times10^9$/l) and increased ESR (36 mm/h) were observed in the blood count. During immunological response assays, a decrease of CD4+ and CD8+ subsets and low lymphocyte blasttransformation responses with PHA and PPD were detected.

After two months of traditional therapy a small improvement in the patient's condition was seen; however, the reoentgenological picture was without significant change and immune responses remained inhibited.

SCV-07 was injected intramuscularly at 0.1 mg, once per day, for 5 days with continued traditional antituberculosis therapy (isoniazid at 600 mg/day intravenously, pyrazinamid at 1500 mg/day per so, rifampicin at 450 mg/day per os, kanamycin at 1000 mg/day intramuscularly). The clinical improvement was significant. Sputum culture tests became negative, cavities closed and infiltrative foci resolved. Immunological responses were close to normal. CD3+ lymphocytes increased from $1.011\times10^9$/l to $1.441\times10^9$/and CD8+ numbers increased from 12% to 21%. A normal range is approximately 26–40%. Lymphocyte functional abilities were also markedly elevated post SCV-07 treatment. Finally, the blasttransformation response with PHA increased from 29% to 40%. A normal level is approximately 50%.

EXAMPLE 3

Patients with destructive lung tuberculosis, untreated previously or after inadequate antituberculosis therapy were treated. All patients received antituberculosis therapy consisting of intravenous isoniazid and four to five other drugs and the condition of each patient was examined daily. Major diagnostic criteria included physical examination, chest X-ray, sputum bacterioscopy and culture, broncho alveolar lavage examination. Also included were blood counts performed in all patients prior to SCV-07 therapy and then once per week. Blood biochemical tests including blood fibrinogen, β-lipoproteins, urea, creatinine, C-reactive protein levels, activity of alanine and asparagine transaminases were performed once per month and more frequently if needed. Sputum cultures were taken prior to therapy and one and three months after SCV-07 therapy, and serologic assays including indirect hemaglutination tests.

Bilateral lung injury was found in 11 patients. Multisegmental damage was observed in 11 cases. Other patients possessed mono- and bi-segmental lung lesions. In all cases, the pathological process was destructive. Cavities from 1 to 8 cm were observed in 17 X-ray films. Immature cavities were diagnosed in 3 cases. Multiple cavities, X-ray markers and exudative inflammation predominated in all patients.

Patients were divided into two comparable groups: 20 patients which were treated with SCV-07 and 15 patients which were the control. Females slightly predominated the experimental group (55%). Patients ranged in age from 20 to 40 years of age. All patients had symptoms of toxemia, including 4 patients with severe symptoms. Eight patients in the experimental group possessed a productive cough.

Typically, the chest X-ray and tomograms prior to SCV-07 treatment indicated an infiltrate-like shadow in the upper lobes. The sixth segment of the right lung was surrounded by small infiltrates. Different multiple foci with periofocal inflammation were in axial and lingual segments of the left lung. Following two months of SCV-07 therapy, the chest X-ray and tomogram indicated a resolution of the infiltrate-like shadow, and foci in both lungs was detected.

SCV-07 treatment in humans increased the efficacy of the antituberculosis therapy in the experimental group. Toxemia symptoms were substantially resolved in half of the patients within a month. Moist rates resolved in 16 patients where body temperature decreased in all cases. Cavity closure after 3 months of observation was observed in 25% of the patients from the experimental group as compared to only 13.3% in the control group. Negative sputum culture tests were observed in 30% of SCV-07 treated patients compared to 13.3% in the control group after a month of observation and in 65% versus 33.3% respectively after 3 months.

Hematological signs of tuberculosis activity including white blood cell counts and ESR were mostly diminished in the experimental group. White blood cell counts of more than $10\times10^9$/L were found in 6 patients and a "left shift" was seen in 7 patients.

A lymphocyte level less than 18% was established in 10 cases and an ESR higher than 40 mm/h was seen in 4 patients. Eosinophil and monocyte levels were close to normal prior to SCV-07 therapy and were unchanged during therapy. Serum bilirubin, creatinine, urea, alanine and asparagine transaminase stabilized. Serum biochemical inflammation markers such as fibrinogen, β-lipoprotein, CRP decreased in one month.

Prior to SCV-07 therapy, a decrease in the parameters of cell immunity was found in patients. A decrease of CD3+ lymphocytes was detected in 9 patients, a decrease in CD4+ production in 1 patient and a decrease in CD8+ production in 10 patients, all out of 14 examined patients.

Immunological studies included counting the percentage of peripheral blood lymphocyte subsets such as CD3+, CD4+, CD8+, CD20+, CD25+ and CD95+ using monoclonal antibodies. The CD4/CD8 index was calculated as well. Elevation of CD3+ and CD4+ cell levels were apparent in 7 out of 14 patients immediately after SCV-07 therapy. The CD4+/CD8+ ratio also increased. These changes significantly improved in SCV-07 treated patients in comparison to those patients in the control group.

Phytohemagglutinin (PHA) and purified protein derivate (PPD)-induced lymphocytes blasttransformation were also investigated. T-cell blasttransformation responses markedly increased in the experimental group compared with those in the control group in comparison to inhibition of the T-lymphocyte blasttransformation response to PHA (44.1±2.4%) observed in 7 patients and an extremely low T-cell response to PPD seen in 6 out of 8 studied cases prior to therapy.

IL-2 production after stimulation with the mitogens PHA and PPD in SCV-07 treated patients greatly increased.

EXAMPLE 4

This example illustrates the effect of immunization with SCV-07 in 200 mice (Lab Animals Nursery, Rappolovo, Russia) prior to challenge with *M. bovis* 8.

SCV-07 was lyophilized in ampules at 0.1 mg per ampule, and stored at +4° C. SCV-07 was reconstituted with 1 ml of 0.9% sodium chloride. To induce infection, mice were injected with a *M. bovis* 8 suspension (0.1 mg in 0.2 ml of physiological saline) into the tail lateral vein. Twelve days later, animals possessing submiliary focuses in lungs after inoculation were randomized to one of seven groups.

Isoniazid therapy (10 mg/kg, subcutaneous) began. Animals with multiple submiliary focuses continued in the study and those animals in groups began treatment with SCV-07 on Day 20 and were provided with 5 daily intraperitoneal (ip) injections. Animals were treated with a second course of SCV-07, 2 days following the first treatment (Day 26) and were provided with 5 additional daily injections. Control groups included mice without therapy (inoculation control) and mice on isoniazid therapy alone (therapy control).

Samples were harvested on days 4, 10, 17 and 24 after SCV-07 therapy. At least 5 mice from each group were examined.

Lung damage was calculated during a macroscopic assay in accordance with the number and severity of specific inflammation foci. Single submiliary foci were estimated at 0.5 units (U), multiple submiliary foci (<20) as 1.0 U, multiple submilliary foci (>20) as 1.5 U, single miliary foci as 1.75 U, multiple associate submiliary and single miliary foci as 2.0 U, miliary foci (<10) as 2.25 U, multiple associated miliary foci as 2.75 U, small caseous foci as 3.0 U, disseminate caseous as 4.0 U, damage to the entire lung as 5.0 U. In the case of lung maceration by serous liquid, the index was increased by 0.25 to 1.0 U, depending on the extent of damage.

Calculation of the weight index (WI) was accomplished according to the formula:

$$WI=\text{organ weight (g) mouse weight (g)}\times100$$

Preliminary experimentation indicated that the particular strain of *M. bovis* 8 possessed low virulence. Confirmation of low virulence included the examination of several factors: (1) the appearance of single lung submiliary foci only on Day 11 and multiple foci on Day 19 after inoculation, (2) no deaths until Day 34 after inoculation, and (3) the severity of infection in un-treated mice on Day 28 was similar to mice with lowly progressive tuberculosis on Day 26.

The use of SCV-07 therapy affects the progression of tuberculosis. SCV-07 treatment at all doses decreased the lung damage index when measured 4 days after the end of 5 days of therapy (Day 28 of infection). Groups 5, 7, 8 and 9 (SVC-07 doses of 1, 0.1, and 0.01 ìg/kg ip and 1 ìg/kg SCV-7 po) in comparison to untreated controls (Group 2) exhibited significant differences. Significant differences were also seen between Group 7 (0.1 ìg/kg ip) and Group 3 (isoniazid control). However, no significant difference occurred between untreated mice (Group 2) and those treated with isoniazid alone (Group 3).

Both 10 days and 17 days after the termination of treatment, differences between the control and experimental groups lacked significance. Only a decrease of the lung damage index in Group 7 (0.1 ìg/kg ip) considerably differed from the control.

Maximum effects of SCV-07 therapy were seen 24 days after the end of therapy. Once again, favorable results were exhibited in Group 7 (0.1 ìg/kg ip). Mice in this group significantly increased in body weight (30.8% versus 20.7% in isoniazid control Group 3), decreased in lung weight index (1.38±0.06 versus 1.07±0.23 in control Group 3) and in spleen weight index (1.59±0.25 versus 1.94±0.31 in Group 3). At this time point, a significant decrease occurred in the growth of *M bovis* cultured from spleens from Group 7 mice (200±0 CFU versus 275±14.1 CFU in Group 3).

It appears that treatment with SCV-07 therapy for 10 injections (Group 6) provided a better response than 5 injections at the same dose (Group 5). The amount of *M. bovis* growth in spleen cultures significantly decreased for Group 6 (190±21.5 CFU versus 275±14.1 CFU in the control. However, this trend did not occur in Group 5, 24 days after treatment.

After decapitation, blood was collected in Petri dishes and slides were prepared immediately, before blood coagulation. Air-dried slides were fixed in 96% ethanol for 10 min and stained by Giemsa stain. On each slide, 100–200 cells were counted and results were expressed as a percentage. For a leukocyte count, 10 ìl of blood was mixed with 190 ìl acetic acid aqueous solution in a 96-well plate (Costar, Cambridge, Mass.), and under 100× magnification and oil immersion. A Goriaev hemocytometer determined the count.

Tuberculosis infection caused a decrease in total blood lymphocyte and an increase in neutrophilic granulocytes as shown in Group 2, the infected control. SCV-07 therapy induced changes in these numbers. Significant changes in treated animals were not observed as early as 4 days after therapy, but 10 days after therapy, a decrease in monocyte levels developed as seen in Groups 6, 7, 8 and 9 (SCV-07 doses of 1 ìg/kg ip; 10 injections; 0.1 ìg/kg ip; 5 injections and 1 ìg/kg po compared with Group 3, the isoniazid control). After 17 days of SCV-07 therapy, an increase in lymphocyte numbers and a significant decrease in percent of neutrophils developed in Groups 8 and 9 (0.01 ìg/kg ip and 1 ìg/kg po). After 24 days, the differences between the Groups were not as evident.

Mice thymuses were collected aseptically, homogenized, suspended in RPMI-1640 medium and filtered through two layers of sterile gauze. Cell suspensions were washed twice in RPMI-1640 with 2 mM L-glutamine and 80 ìl/ml gentamycin, then counted using a Goriaev hemocytometer.

No significant differences in basal thymic cell proliferation between SCV-07 treated (Groups 4 to 9) and control (Groups 1 to 3) mice occurred. On the other hand, after 4 days of therapy, Con A stimulated thymic cell proliferation exhibited numbers significantly higher for Group 7 (SCV-07 dose of 0.1 ìg/kg ip) in comparison to Group 3 (isoniazid control). Differences in other groups were not evident. Proliferation increased in all groups at later time points, but proliferation was significantly higher in SCV-07 treated groups. By day 17, the proliferation response in Groups 7 and 8 (0.1 and 0.01 ìg/kg ip) showed essentially the same response as uninfected mice. By day 24, proliferation in Groups 6, 7 and 8 (1 ìg/kg, 10 injections ip, and 0.1 and 0.01 ìg/kg ip) exhibited similarities to uninfected mice and higher numbers than the isoniazid control Group 3.

Spleens from mice were harvested aseptically, homogenized in RPMI-1640 medium (Biolot, Russia) and filtered through two layers of sterile gauze. Erythrocytes were lysed in 0.83% percent ammonium chloride solution after centrifugation of the homogenate. Spleen cells were washed twice with RPMI-1640 with 2 mM L-glutamine and 80 ìl/ml gentamycin (Sigma, St. Louis, Mo.), then counted using a Goriaev hemocytometer.

Seventeen days after SCV-07 therapy, an increase in lymphocyte production and a significant decrease in the percentage of neutrophils developed in Groups 8 and 9 (0.01 ìg/kg ip and 1 ìg/kg po). After 24 days of SCV-07 therapy, the differences between the groups were not as evident.

Spleen cell proliferation data is presented. Restoration of the mitogen (Con A and LPS) induced response in SCV-07 treated animals occurs sooner than the isoniazid treated animals. After 24 days of SCV-07 therapy, proliferative response with LPS in Group 6 (1 ìg/kg, 10 injections ip) and with Con A in Groups 6 and 7 (1 ìg/kg, 10 injections ip and 1 ìg/kg ip) did not differ from uninfected mice. Meanwhile, in Group 3 the isoniazid control group, the proliferative response remained low.

The spleen cell proliferative response to tuberculin remained low in all groups after 4 days of therapy, but later the proliferative response of Group 6 (1 ìg/kg ip, 10 injections) was significantly higher than the control.

Spleen cells and thymic cells were isolated as described above. In vitro, thymic cells were diluted to $10^7$/ml in RPMI-1640 with 2 mM L-glutamine, 80 ìg/ml gentamycin and 4% heat-inactivated fetal calf serum (Sigma, St. Louis, Mo.). Spleen cells were diluted to $3\times10^6$/ml in RPMI-1640 with 2 mM L-glutamine, 80 ìg/ml gentamycin and 20% inactivated fetal calf serum. 0.5 ìg/ml Concanavalin A (Con A, Sigma, St. Louis, Mo.) was used to stimulate thymic cell proliferation. For spleen cell proliferation, 0.5 ìg/ml Con A, 10 ìg/ml lipopolysaccharide (Sigma, St. Louis, Mo.), and 50 ìg/ml tuberculin purified protein derivative (PPD) were utilized. The assay was carried out in 96-well plates and cell cultures were incubated for 72 hours, or 96 hours if tuberculin was used, at 37° C. in humidified 5% $CO_2$, then pulsed with 5 ìl Ci/ml $^3$H-thymidine overnight (approximately 16 h) and harvested on filters using a semi-automated harvester (Titertek™, Flow Laboratories, Norway). Filters were dried and proliferation calculated by $^3$H-thymidine incorporation by counting samples in a liquid scintillation counter (LKB 1217 Racketa, Wallace, Sweden). Data was expressed in impulses per minute.

In order to study phagocytosis, peritoneal macrophages were plated at a concentration of $10^6$ cells per Petri dish and media including $10^7$ *Saccharomyces cerevisiae* cells, opsonized by mice serum was added. Results were evaluated using the Mann-Whitney test. Phagocytic activity was calculated after determination of percentage of macrophages involved in phagocytes. The phagocytic index was determined by calculating the average number of yeast phagocytosed per one cell. Killing activity was resolved by the number of yeast digested by macrophages after 1.5 h of incubation. Finally, the killing index was determined as follows:

$$KI = \frac{\text{phagocytic index after 1 hr}}{\text{phagocytic index after 2.5 hr}}$$

Infection with tuberculosis leads to a decrease in peritoneal phagocytic activity, phagocytic index and phagocytic killing of yeast cells. After infection, the average phagocytic activity on Day 28 was 4.6% as compared to 64.2% in uninfected mice ($p\leqq0.01$). Phagocytic killing decreased 2-fold. Isoniazid therapy increased these phagocytic activity indexes but not to the level as seen in uninfected mice. After 4 days treatment, SCV-07 therapy markedly elevated phagocytic activity to 38.8% in Group 7 (SCV-07 dose of 0.1 ìg/kg ip) compared to 19.4% in Group 3 (isoniazid control group, $p\leqq0.05$). SCV-07 treatment also normalized the phagocytic index and increased killing (244.4 versus 196.4 in control, $p\leqq0.05$).

Ten days after SCV-07 therapy, a lesser effect of the drug was observed, perhaps as a result of the isoniazid therapy. Killing significantly increased compared to the control only in Group 5 (1 ìg/kg, ip). A tendency toward decreased ingestion and killing in groups of animals that displayed minimum efficacy of the drug toward severity of tuberculosis existed (Groups 8 and 9, 0.01 ìg/kg ip and 1 ìg/kg po).

After 17 days of SCV-07 therapy in mice, a decrease of ingestion and killing in Group 3 (isoniazid control). All SCV-07 treated mice exhibited increased phagocytic indexes more notably in Group 6 (1.0 ìg/kg ip, 10 injections). The level of phagocytic activity in this group remained the same as uninfected mice (60.4% versus 49.8% in Group 3) and phagocytic index (6.88 U versus 4.91 U, p=0.05). Both killing and the killing index significantly increased and a trend toward increased phagocytic function in other SCV-07 treatment groups was evident.

Phagocytosis in the isoniazid treatment group returned to the level seen in uninfected mice at 24 days after treatment. However, a decrease in phagocytic killing still existed (62.0 U in Group 3 versus 178.0 in uninfected mice, p=0.05). Possibly, this was an immunosuppressive effect of isoniazid leading to a decrease in macrophage killing. SCV-07 treatment, particularly in Groups 6 and 7 (1.0 ìg/kg, 10 injections and 0.1 ìg/kg ip), significantly improved macrophage killing.

Mice peritoneal cells were harvested through peritoneal cavity washing with a liquid consisting of Eagle medium (Biolot, Russia) with 10% fetal calf serum and 10 IU/ml heparin. Counted cells and cell suspensions were placed in 96-well plates (100 ìl/well). After plates were incubated for 1 h at 37° C. in humidified $CO_2$, the supernatant was removed and the adherent cell monolayer washed 3 times with warm (37° C.) Eagle medium, dried, and then fixed and stained by 0.03% solution of crystal-violet in 30% methanol. A plate reader allowed for plates to be read at 595 nm and results were expressed as the extinction coefficient (related to cell number in the sample).

Peritoneal cell suspensions in Eagle media were centrifuged at 1200 rpm. The media was decanted, cells were washed in 0.9% saline solution and resuspended in 0.1% NBT HBSS solution at pH 7.2. These reactions occurred in 96-well plates. The counted cells were placed in the wells in a volume of 100 ìl and incubated at 37° C. in humidified $CO_2$ for 1 h. After incubation, the supernatant was decanted, plates were dried at room temperature and cells were fixed in 70% methanol. In a solution of 2 M potassium hydroxide and 140 ìl DMSO, diformazane was added. Using a plate reader, plates were read at 640 nm and results were expressed as the extinction coefficient (related to cell number in the sample).

In RPMI-1640, spleen cells were diluted to a concentration of $10^7$/ml with 10% fetal calf serum, 2 mM L-glutamine and 80 ìg/ml gentamycin. A 100 ìl cell suspension was added to each well of a 96-well culture plate and cytokine production was induced by Con A at a final concentration of 2.5 ìg/ml. A control well included RPMI-1640. For 24 hours, cells were incubated at 37° C. and humidified in 5% $CO_2$. Following incubation, 150 ìl of supernatant was removed from each well and stored at −70° C.

In order to determine the IL-2 concentration in cell culture supernatants, the CTLL-2 IL-2 dependent cell line was used. CTLL-IL-2 cells were washed twice in RPMI-1640 and counted with a Goriaev hemocytometer. Supernatants were diluted in 96-well culture plates at dilutions of 1:5, 1:15, 1:45 and 1:135 in a volume of 100 ìl. IL-2 standard dilutions were also prepared. Cells were diluted to 2×105/ml in RPMI-1640 with 10% inactivated fetal calf serum, 2 mM L-glutamine, 80 ìg/ml gentamycin. The 100 ìl suspension was added to each well of the culture plate and incubated for 48 h at 37° C. in 5% $CO_2$ humidity. Ten ìl of 5 ì Ci/ml $^3$H-thymidine was added to each well 16 h before the end of incubation. Following incubation, the cells were harvested on filters through the use of a semi-automated harvester and samples were counted in a liquid scintillation counter.

A decrease of production of IL-2 in Con A stimulated spleen cells after tuberculosis infection occurred. On the other hand, an increase in IL-2 production was observed in all treated groups, at all time points after therapy. As early as 4 days after SCV-07 therapy, IL-2 production markedly increased in Groups 7 and 8 (SVC-07 doses of 0.1 and 0.01 ìg/kg ip) as compared to Group 3 (41.6±5.6 U/ml and 39.1±2.8/ml versus 16.6±2.6 U/ml, respectively). As of 24 days after SCV-07 therapy, the IL-2 level in Group 6 (1 ìg/kg ip, 10 injections) and Group 7 (0.1 ìg/kg ip) did not differ from uninfected mice.

IL-4 and INF-γ assays in Con A-stimulated spleen cell supernatants were also performed using Quantikine™ ELIZA kits R & D Systems, Minneapolis, Minn.) in accordance with kit instructions. Plates were coated with monoclonal antibodies to either IL-4 or IFN-γ and blocked. Standards and samples were subsequently added. The cells were incubated for 2 h and washed, following with the addition of a colorimetric substrate. After 30 minutes, the reaction was terminated and plates were read at 450 nm using a plate reader (Multiscan™ 3550, BioRad, Japan).

Basal IFN-γ production 4 days after SCV-07 therapy failed to differ from isoniazid control mice (Group 3). Ten days after SCV-07 therapy however, a significant elevation of basal IFN-γ production in Groups 5, 6 and 7 (SCV-07 doses of 1 ìg/kg ip, 5 injections; 1 ìg/kg ip, 10 injections and 0.1 ìg/kg ip) occurred. At 17 days after SCV-07 therapy, this increase was observed in all mice. At the end of the experiment maintenance of this increase in INF-γ production was seen only in Group 6 (1 ìg/kg ip, 10 injections).

No significant changes in basal IL-4 production occurred. Con A stimulated the production of IFN-γ and IL-4. Notably, IL-4 and IFN-γ production were changed in opposite directions. At 10 days after SCV-07 therapy, INF-γ production exhibited stimulation in Groups 4, 5, 6 and 8 (10 and 1 ìg/kg ip, 5 injections; 1 ìg/kg ip, 10 injection 0.01 ìg/kg ip ip) and IL-4 production significantly decreased in Groups 5, 6 and 7 (1 ìg/kg ip, 5 injections; 1 ìg/kg ip/10 injections, and 0.1 ìg/kg ip).

INF-γ and IL-4 concentrations in blood serum. After 10 days of SCV-07 therapy, IFN-γ levels increased in Groups 4, 5, 6 and 7 (10 and 1 ìg/kg ip, 5 injections; 1 ìg/kg ip, 10 injections; and 0.1 ìg/kg ip) while IL-4 levels decreased in the same groups. These changes also similarly occurred after 17 days of SCV-07 therapy. The concentration of IFN-γ increased in Groups 4, 5, 6, 7 and 8 (significantly in group 7 and 8, 0.1 and 0.01 ìg/kg ip) and simultaneously, IL-4 significantly decreased in Groups 5, 6 and 7 (1 ìg/kg ip, 5 injections; 1 ìg/kg ip, 10 injections; and 0.1 ìg/kg ip).

In mice, SCV-07 treatment during isoniazid tuberculosis therapy influences the severity of the disease and the strength of the immune response. SCV-07 provided in 5 daily ip injections at a dose of 0.1 ìg/kg significantly decreases both the lung weight index and the lung damage index. *M. bovis* growth in spleen culture also decreases in these mice as well as mice treated with 10 daily injections at a dose of 1.0 ìg/kg and mice treated with 5 daily injections of 0.01 ìg/kg.

Improvement in Con A stimulated thymic cell proliferation is seen as early as 4 days after SCV-07 treatment. At 10 days after SCV-07 therapy, prolific results are seen for proliferation stimulated by LPS or tuberculin. At 24 days after SCV-07 treatment, proliferative responses for both thymic and spleen cells are restored to nearly the uninfected animal responses.

SCV-07 stimulation of macrophage function occurs, but an improvement of ingesting and killing ability which had been decreased by tuberculosis infection and isoniazid therapy occurs. Production of cytokines, another measure of the immune response, increases with the treatment of SCV-07. Production of IL-2 by spleen cells decreases from infection with tuberculosis; however, a significantly less reduction 4 days after SCV-07 treatment occurs in certain groups. After 24 days of treatment, production of IL-2 in other groups is restored to the uninfected animal level.

Finally, both basal and stimulated INF-γ production by both thymic and spleen cells increase after SCV-07 treatment. At certain time points, IL-4 production decreases in these same mice. Con A stimulated production of IL-4 decreases in certain groups and serum levels of IL-4 also reflect this change. These changes, increase of INF-γ and a decrease of IL-4 production, suggest that SCV-07 treatment is providing a shift from a T-helper cell response to a Th1-like immune response.

Although the present invention has been described in some detail by way of illustration and example for purposes of clarity of understanding, changes and modifications can be carried out without departing from the scope of the invention which is intended to be limited only by the scope of the appended claims.

We claim the following:

1. A method for treating tuberculosis in an animal, which comprises administering to an animal with tuberculosis a therapeutically effective amount of an immunomodulator of Formula A:

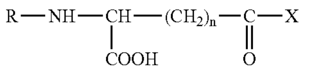

(A)

wherein n is 1 or 2, R is hydrogen, acyl, alkyl or a peptide fragment, and X is an aromatic or heterocyclic amino acid or a derivative thereof.

2. The method of claim 1, wherein R is hydrogen, an acyl having 2 to about 10 carbon atoms, or an alkyl having from 1 to about 6 carbons, and X is L-tryptophan or D-tryptophan, and wherein the carbon of the CH group shown in Formula A has a stereoconfiguration, when n is 2, that is different from the stereoconfiguration of X.

3. The method of claim 2 wherein X is L-tryptophan.

4. The method of claim 1, wherein said immunomodulator is selected from the group consisting of γ-D-glutamyl-L-tryptophan, γ-L-glutamyl-L-tryptophan, γ-L-glutamyl-$N_{in}$-formyl-L-tryptophan, N-methyl-γ-L-glutamyl-L-tryptophan, N-acetyl-γ-L-glutamyl-L-tryptophan, γ-L-glutamyl-D-tryptophan, β-L-aspartyl-L-tryptophan, and β-D-aspartyl-L-tryptophan.

5. The method of claim 1 wherein said immunomodulator is γ-D-glutamyl-L-tryptophan (SCV-07).

6. The method of claim 1 wherein said immunomodulator is administered at a dosage within a range of about 0.001–10 mg.

7. The method of claim 1 wherein said immunomodulator is administered at a dosage within a range of about 0.01–1 m.

8. The method of claim 5 wherein said SCV-07 is administered at a dosage within a range of about 0.01–1 mg.

9. The method of claim 8 wherein said dosage is about 0.1 mg.

10. The method of claim 1, further comprising administration of a therapeutically effective amount of an antimicrobial compound effective against tuberculosis wherein said antimicrobial compound is selected from the group consisting of isoniazid, pyrazinamid, rifampicin, kanamycin, ethambutol, streptomycin, capreomicin, amicacin and cycloserine.

11. The method of claim 10 wherein said therapeutically effective amount of antimicrobial compound is a dosage within a range of about 100–10,000 mg.

12. The method of claim 10 wherein said therapeutically effective amount of antimicrobial compound is a dosage within a range of about 200 to 2,000 mg.

13. The method of claim 10 wherein said therapeutically effective amount of antimicrobial compound is a dosage within a range of about 400 to 1,000 mg.

14. The method of claim 1 wherein the animal is a human patient.

* * * * *

UNITED STATES PATENT AND TRADEMARK OFFICE
CERTIFICATE OF CORRECTION

PATENT NO. : 7,173,013 B2
APPLICATION NO. : 10/485487
DATED : February 6, 2007
INVENTOR(S) : Kolobov et al.

It is certified that error appears in the above-identified patent and that said Letters Patent is hereby corrected as shown below:

| Column | Line | Correction |
|---|---|---|
| 6 | 27 | First occurrence: Change “ìg/kg” to --μg/kg--<br>Second occurrence: Change “ìg/kg” to --μg/kg-- |
| 6 | 30 | Change “ìg/kg” to --μg/kg-- |
| 6 | 37 | Change “ìg/kg” to --μg/kg-- |
| 6 | 41 | Change “ìg/kg” to --μg/kg-- |
| 6 | 61 | First occurrence: change “ìl” to --μl--<br>Second occurrence: change “ìl” to --μl-- |
| 7 | 5 | First occurrence: change “ìg/kg” to --μg/kg--<br>Second occurrence: change “ìg/kg” to --μg/kg-- |
| 7 | 6 | Change “ìg/kg” to --μg/kg-- |
| 7 | 9 | Change “ìg/kg” to --μg/kg-- |
| 7 | 10 | Change “ìg/kg” to --μg/kg-- |
| 7 | 15 | Change “ìl/ml” to --μg/ml-- |
| 7 | 22 | Change “ìg/kg” to --μg/kg-- |
| 7 | 27 | Change “ìg/kg” to --μg/kg-- |
| 7 | 29 | Change “ìg/kg” to --μg/kg-- |
| 7 | 30 | Change “ìg/kg” to --μg/kg-- |
| 7 | 37 | Change “ìl/ml” to --μg/ml-- |
| 7 | 43 | First occurrence: Change “ìg/kg” to --μg/kg--<br>Second occurrence: Change “ìg/kg” to --μg/kg-- |
| 7 | 49 | Change “ìg/kg” to --μg/kg-- |

UNITED STATES PATENT AND TRADEMARK OFFICE
CERTIFICATE OF CORRECTION

PATENT NO. : 7,173,013 B2
APPLICATION NO. : 10/485487
DATED : February 6, 2007
INVENTOR(S) : Kolobov et al.

It is certified that error appears in the above-identified patent and that said Letters Patent is hereby corrected as shown below:

| **Column** | **Line** | **Correction** |
|---|---|---|
| 7 | 50 | Change "ìg/kg" to --μg/kg-- |
| 7 | 51 | Change "ìg/kg" to --μg/kg-- |
| 7 | 56 | Change "ìg/kg" to --μg/kg-- |
| 7 | 60 | Change "ìg/ml" to --μg/ml-- |
| 7 | 63 | Change "ìg/ml" to --μg/ml-- |
| 7 | 64 | Change "ìg/ml" to --μg/ml-- |
| 7 | 66 | Change "ìg/ml" to --μg/ml-- |
| 7 | 67 | Change "ìg/ml" to --μg/ml-- |
| 8 | 1 | Change "ìg/ml" to --μg/ml-- |
| 8 | 5 | Change "ìl Ci/ml" to --μCi/ml-- |
| 8 | 39 | Change "ìg/kg" to --μg/kg-- |
| 8 | 48 | Change "ìg/kg" to --μg/kg-- |
| 8 | 51 | First occurrence: Change "ìg/kg" to --μg/kg--<br>Second occurrence: Change "ìg/kg" to --μg/kg-- |
| 8 | 55 | Change "ìg/kg" to --μg/kg-- |
| 9 | 1 | Change "ìg/kg" to --μg/kg-- |
| 9 | 2 | Change "ìg/kg" to --μg/kg-- |
| 9 | 8 | Change "ìl/well" to --μl/well-- |
| 9 | 21 | Change "ìl" to --μl-- |

UNITED STATES PATENT AND TRADEMARK OFFICE

CERTIFICATE OF CORRECTION

PATENT NO. : 7,173,013 B2
APPLICATION NO. : 10/485487
DATED : February 6, 2007
INVENTOR(S) : Kolobov et al.

It is certified that error appears in the above-identified patent and that said Letters Patent is hereby corrected as shown below:

| Column | Line | Correction |
|---|---|---|
| 9 | 25 | Change “ìl” to --µl-- |
| 9 | 31 | Change “ìg/ml” to --µg/ml--<br>Change “ìl” to --µl-- |
| 9 | 34 | Change “ìg/ml” to --µg/ml-- |
| 9 | 36 | Change “ìl” to --µl-- |
| 9 | 43 | Change “ìl.” to --µl.-- |
| 9 | 46 | Change “ìg/ml” to --µg/ml--<br>Change “ìl” to --µl-- |
| 9 | 48 | Change “ìl” to --µl--<br>Change “ì Ci/ml” to --µCi/ml-- |
| 9 | 59 | Change “ìg/kg” to --µg/kg-- |
| 9 | 61 | Change “ìg/kg” to --µg/kg-- |
| 9 | 62 | Change “ìg/kg” to --µg/kg-- |
| 10 | 11 | First occurrence: Change “ìg/kg” to --µg/kg--<br>Second occurrence: Change “ìg/kg” to --µg/kg-- |
| 10 | 12 | Change “ìg/kg” to --µg/kg-- |
| 10 | 15 | Change “ìg/kg” to --µg/kg-- |
| 10 | 20 | Change “ìg/kg” to --µg/kg-- |
| 10 | 21 | Change “ìg/kg” to --µg/kg--<br>Change “ìg/kg ip ip” to --µg/kg ip-- |
| 10 | 23 | First occurrence: Change “ìg/kg” to --µg/kg--<br>Second occurrence: Change “ìg/kg” to --µg/kg-- |

UNITED STATES PATENT AND TRADEMARK OFFICE

CERTIFICATE OF CORRECTION

PATENT NO. : 7,173,013 B2
APPLICATION NO. : 10/485487
DATED : February 6, 2007
INVENTOR(S) : Kolobov et al.

It is certified that error appears in the above-identified patent and that said Letters Patent is hereby corrected as shown below:

| Column | Line | Correction |
|---|---|---|
| 10 | 24 | Change “ìg/kg” to --μg/kg-- |
| 10 | 27 | First occurrence: Change “ìg/kg” to --μg/kg--<br>Second occurrence: Change “ìg/kg” to --μg/kg-- |
| 10 | 28 | Change “ìg/kg” to --μg/kg-- |
| 10 | 32 | Change “ìg/kg” to --μg/kg-- |
| 10 | 33 | Change “ìg/kg” to --μg/kg-- |
| 10 | 34 | First occurrence: Change “ìg/kg” to --μg/kg--<br>Second occurrence: Change “ìg/kg” to --μg/kg-- |
| 10 | 38 | Change “ìg/kg” to --μg/kg-- |
| 10 | 42 | Change “ìg/kg” to --μg/kg-- |
| 10 | 43 | Change “ìg/kg” to --μg/kg-- |
| 12 | 11 | In claim 7, change “m.” to --mg.-- |

Signed and Sealed this

Twelfth Day of May, 2009

JOHN DOLL
*Acting Director of the United States Patent and Trademark Office*